United States Patent
Powell et al.

(10) Patent No.: US 7,488,372 B2
(45) Date of Patent: Feb. 10, 2009

(54) PROCESS FOR INHIBITING DEPOSITION OF SOLIDS FROM A GASEOUS STREAM

(75) Inventors: Joseph Broun Powell, Houston, TX (US); Robert Earl Hammond, Houston, TX (US)

(73) Assignee: Shell Oil Company, Houston, TX (US)

(*) Notice: Subject to any disclaimer, the term of this patent is extended or adjusted under 35 U.S.C. 154(b) by 620 days.

(21) Appl. No.: 11/344,843

(22) Filed: Feb. 1, 2006

(65) Prior Publication Data
US 2006/0189831 A1 Aug. 24, 2006

Related U.S. Application Data

(60) Provisional application No. 60/649,642, filed on Feb. 3, 2005.

(51) Int. Cl.
B01D 19/00 (2006.01)
B01D 53/14 (2006.01)
B01D 53/64 (2006.01)

(52) U.S. Cl. ............ 95/133; 95/258; 95/158; 95/266; 95/265; 95/257; 210/750; 568/456

(58) Field of Classification Search .......... 95/258, 95/158, 133, 266, 265, 257; 210/750; 568/456
See application file for complete search history.

(56) References Cited

U.S. PATENT DOCUMENTS

| | | | |
|---|---|---|---|
| 2,757,205 A * | 7/1956 | Mertzweiller et al. ...... 568/456 |
| 2,779,794 A | 1/1957 | Catterall ............... 260/604 |
| 3,188,351 A * | 6/1965 | Lemke ................ 568/456 |
| 3,868,422 A | 2/1975 | Hart et al. ............. 260/604 |
| 3,966,886 A | 6/1976 | Bakker ................ 423/417 |
| 4,041,057 A | 8/1977 | Fanning .............. 260/410.9 |
| 4,234,545 A | 11/1980 | El-Chahawi et al. ....... 423/138 |
| 4,625,067 A | 11/1986 | Hanin ................. 568/451 |
| 5,237,105 A | 8/1993 | Summerlin ............ 568/451 |
| 5,451,384 A | 9/1995 | Carr .................. 423/210 |

(Continued)

FOREIGN PATENT DOCUMENTS

DE 1965440 8/1970

(Continued)

OTHER PUBLICATIONS

Mechanism of the Reaction Involving the Formation of Dioxane Byproduct During the Production of Poly(ethylene Terephthalate), A.V. Popoola, J. Applied Polymer Sci., vol. 43, 1875-1877 (1991).

(Continued)

*Primary Examiner*—Duane S Smith
*Assistant Examiner*—Douglas J Theisen

(57) ABSTRACT

The present invention relates to a process for degassing an aqueous solution containing a hydroformylation product and separating a volatile metal species from gaseous stream to inhibit or prevent deposition of a solid material from the gaseous stream. To separate the volatile metal species from the gaseous stream, the gaseous stream is either 1) contacted with a liquid that separates the volatile metal species, or a reaction product thereof, from the gaseous stream; 2) passed through a microfilter having a pore size of 2 μm or less; or 3) contacted with an adsorbent material.

14 Claims, 2 Drawing Sheets

U.S. PATENT DOCUMENTS

| | | | |
|---|---|---|---|
| 5,457,240 A | 10/1995 | Beadle et al. | 568/451 |
| 5,463,144 A | 10/1995 | Powell et al. | 568/867 |
| 5,463,145 A * | 10/1995 | Powell et al. | 568/867 |
| 5,463,146 A * | 10/1995 | Slaugh et al. | 568/862 |
| 5,545,765 A | 8/1996 | Slaugh et al. | 568/862 |
| 5,545,766 A | 8/1996 | Powell et al. | 568/862 |
| 5,545,767 A | 8/1996 | Weider et al. | 568/867 |
| 5,563,302 A | 10/1996 | Weider et al. | 568/862 |
| 5,576,471 A | 11/1996 | Semple et al. | 568/862 |
| 5,585,528 A | 12/1996 | Powell et al. | 568/862 |
| 5,689,016 A | 11/1997 | Weider et al. | 568/862 |
| 5,723,389 A | 3/1998 | Slaugh et al. | 468/862 |
| 5,731,478 A | 3/1998 | Slaugh et al. | 568/862 |
| 5,777,182 A | 7/1998 | Powell et al. | 568/862 |
| 5,786,524 A * | 7/1998 | Powell et al. | 568/862 |
| 5,841,003 A | 11/1998 | Slaugh et al. | 568/867 |
| 5,981,808 A | 11/1999 | Powell et al. | 568/862 |
| 5,986,145 A | 11/1999 | Powell et al. | 568/449 |
| 6,130,351 A | 10/2000 | Stern et al. | 562/17 |
| 6,165,428 A | 12/2000 | Eijkhoudt et al. | 423/210 |
| 6,323,374 B1 | 11/2001 | Han | 568/483 |
| 6,376,720 B1 | 4/2002 | Han | 568/483 |
| 6,376,724 B1 | 4/2002 | Han | 568/867 |
| 6,403,836 B2 | 6/2002 | Kaizik et al. | 568/451 |
| 6,684,214 B2 | 1/2004 | Bata et al. | 707/10 |
| 2003/0032845 A1 | 2/2003 | Han et al. | 568/862 |
| 2004/0087819 A1 | 5/2004 | Powell et al. | 568/862 |

FOREIGN PATENT DOCUMENTS

| | | |
|---|---|---|
| GB | 2055371 | 3/1981 |
| SU | 994461 | 2/1983 |
| WO | 93/24437 | 12/1993 |
| WO | WO 9422563 A1 * | 10/1994 |
| WO | 97/16250 | 5/1997 |
| WO | 97/33851 | 9/1997 |
| WO | 01/90690 | 2/2001 |
| WO | WO 2004031108 A1 * | 4/2004 |

OTHER PUBLICATIONS

J. Falbe, New Synthesis with Carbon Monoxide, Springer-Verlang, Berlin, Heidelburg, New York, pp. 164-165 (1980).

* cited by examiner

PROCESS FOR INHIBITING DEPOSITION OF SOLIDS FROM A GASEOUS STREAM

CROSS-REFERENCE TO RELATED APPLICATIONS

This application claims priority to U.S. Provisional Application 60/649,642 filed on Feb. 3, 2005, herein incorporated by reference in its entirety.

FIELD OF THE INVENTION

The present invention relates to a process for inhibiting or preventing deposition of a solid material from a gaseous stream. In particular, the present invention relates to a process for inhibiting or preventing deposition of a solid material from a gaseous stream obtained by at least partially degassing an aqueous mixture separated from a hydroformylation reaction mixture.

BACKGROUND OF THE INVENTION 1,3-propanediol (PDO) is an industrially important chemical. PDO is used as a monomer unit to form polymers such as poly (trimethylene terephthalate) that are used in the production of carpets and textiles. PDO is also useful as an engine coolant, particularly in cooling systems that require coolants having low conductivity and low corrosivity.

PDO may be prepared industrially by hydroformylation of ethylene oxide under pressure in the presence of syngas (CO and $H_2$) and a catalyst to prepare 3-hydroxypropionaldehye (HPA), followed by the hydrogenation of HPA to PDO. Preferred hydroformylation catalysts are metal carbonyls, especially cobalt carbonyl. The hydroformylation reaction is typically conducted in a solvent that is inert to the reactants, that will solubilize carbon monoxide and the catalyst, that is essentially immiscible in water, and that exhibits low to moderate polarity such that the hydroformylation product HPA can be extracted from the solvent with water. Such solvents include ethers such as methyl-t-butyl ether (MTBE), ethyl-t-butyl ether, diethyl ether, phenylisobutyl ether, ethyoxyethyl ether, diphenyl ether, and diisopropyl ether.

Following hydroformylation, the HPA is extracted and separated from the non-water miscible solvent with water. The separated aqueous solution of HPA is then hydrogenated to form PDO in the presence of a hydrogenation catalyst. The organic phase containing the hydroformylation reaction solvent and most of the metal carbonyl catalyst can be recycled to be reused in further hydroformylation.

The separated aqueous solution of HPA may be treated to remove species that can interfere with the performance of the hydrogenation catalyst in the conversion of HPA to PDO. The separated aqueous HPA solution typically contains from 4 to 60 wt. % HPA, residual syngas (including carbon monoxide), residual ethylene oxide, and residual metal carbonyl species from the hydroformylation reaction catalyst such as cobalt or rhodium carbonyl species including $Co[Co(CO)_4]_2$, $Co_2(CO)_8$, and $Rh_6(CO)_{16}$. Most hydrogenation catalysts are poisoned by carbon monoxide (CO) and the residual metal carbonyl species, so the aqueous solution of HPA is treated to remove these catalyst poisons from the solution. The aqueous solution of HPA may be degassed, oxidized and stripped, and then contacted with an acidic ion exchange resin to remove these hydrogenation catalyst poison sources.

The aqueous HPA solution may be degassed, oxidized, and stripped by passing an oxygen containing gas through a column or tank of the aqueous HPA solution—typically in a countercurrent flow arrangement. The pressure maintained on the aqueous HPA solution in the degasser-oxidizer-stripper column or tank is usually lower than the pressure in the hydroformylation reaction and extraction, so that CO gas is flashed from the aqueous HPA solution in the degasser-oxidizer-stripper column or tank, and any residual CO gas is stripped from the solution by the oxygen containing gas and any other stripping gas stream such as nitrogen.

The oxygen containing gas also oxidizes residual metal carbonyl species in the aqueous solution, ensuring that the metal species are water soluble, particularly in the presence of byproduct organic acids such as 3-hydroxypropionic acid in the aqueous HPA solution. The water soluble metal species are removed from the aqueous solution of HPA by contacting the solution with an acidic ion exchange resin.

The gaseous stream containing the degassed CO may be removed from the degasser-oxidizer-stripper tank or column to separate the CO from the aqueous HPA solution. The gaseous stream removed from the degasser-oxidizer-stripper is typically collected and condensed to recover any residual hydroformylation solvent contained therein. Recovery of the solvent from the gaseous stream is important to reduce environmental impact—for example, residual solvent MTBE cannot be vented directly to the atmosphere, as it is a regulated pollutant. The gaseous stream from the degasser-oxidizer-stripper may be compressed using a compressor, and the solvent may be recovered by chilling the compressed gas in a chilling tank.

It has been found that unexpected deposition of solids from the gaseous stream inhibits the efficient recovery of solvent from the gas phase. For example, where gas compression is used for solvent recovery solids deposit in the compressor, thereby fouling the compressor. As a result, the compressor works for only a short period of time before clogging with the deposited solids. The degasser-oxidizer-stripper and other portions of the process must then be shut down to clean or replace the compressor—which results in particularly poor process efficiency, especially in a continuous industrial operation. Further, the compressor suffers undue wear as a result of fouling by the deposited solids. For other solvent recovery configurations such as solvent recovery by liquid phase absorption, distillation, low temperature condensation, or solid adsorption, similar fouling may be observed due to the solids deposited from the gaseous stream.

SUMMARY OF THE INVENTION

The present invention provides a process for inhibiting or preventing deposition of a solid material from a gaseous stream obtained from an aqueous mixture separated from a hydroformylation reaction mixture, comprising separating a volatile metal species from a gaseous stream obtained by at least partially degassing an aqueous mixture separated from a hydroformylation reaction mixture. In one embodiment of the invention, the volatile metal species is separated from the gaseous stream by contacting the gaseous stream with a trapping liquid. In another embodiment of the invention, the volatile metal species is separated from the gaseous stream by passing the gaseous stream through a filter having a pore size of 2 μm or less. In yet another embodiment of the invention,

DETAILED DESCRIPTION OF THE INVENTION

Figure 1:
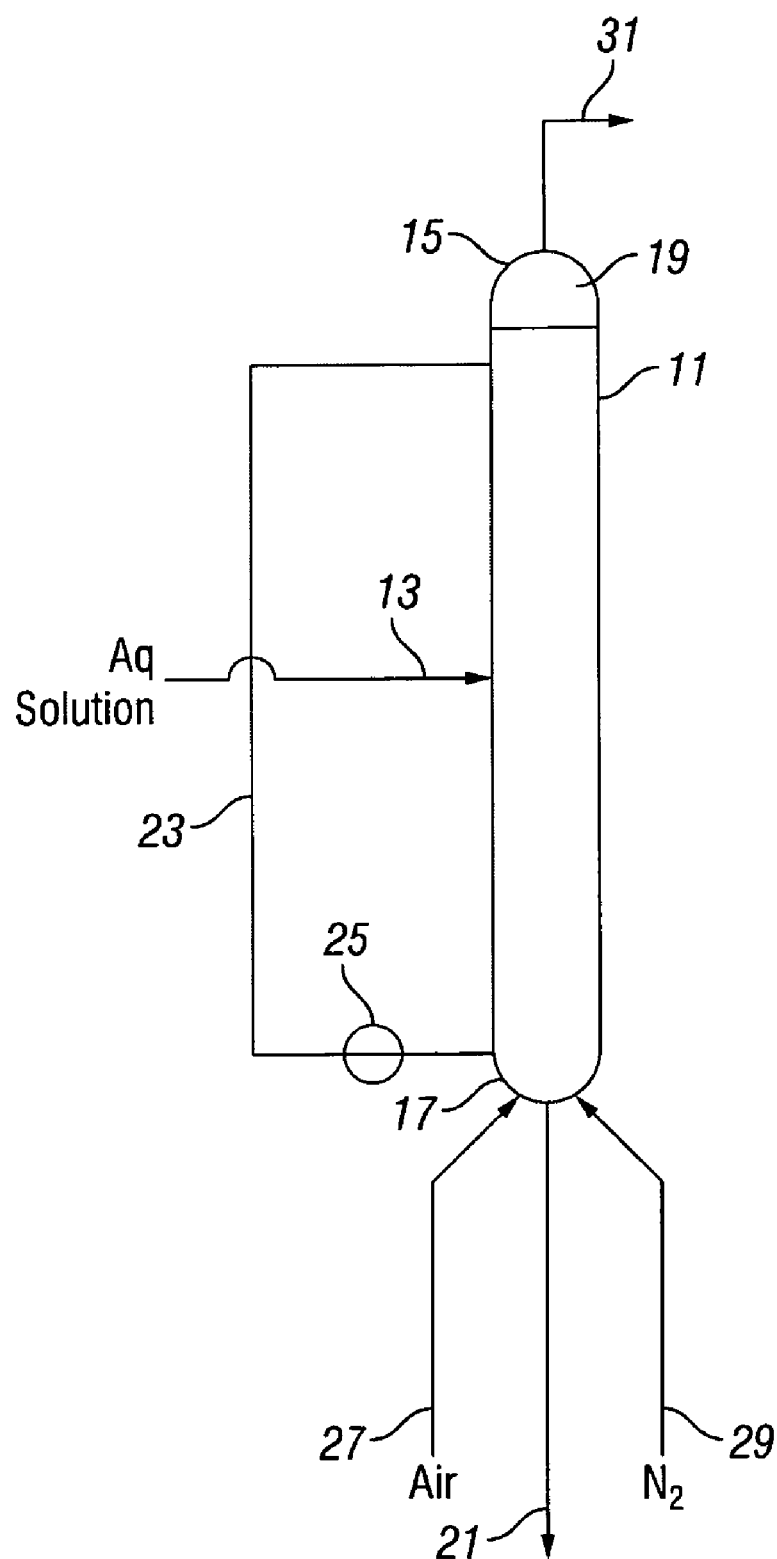
FIG. 1 is a schematic representation of a degasser-oxidizer-stripper column for use in accordance with the process of the present invention.

The present invention provides a process for inhibiting and/or preventing deposition of a solid material from a gaseous stream obtained by at least partially degassing an aqueous mixture separated from a hydroformylation reaction mixture. The presence of a component in the gaseous stream that deposits as a solid at, or near, ambient temperature and at, or near, atmospheric pressure is unexpected since the gaseous stream contains mostly carbon monoxide from the aqueous mixture and oxidizing and stripping gasses such as air and nitrogen. It has been discovered that a volatile metal species is present in the gaseous stream, and the volatile metal species or a reaction product thereof deposits as a solid material from the gaseous stream. The presence of volatile metal species in the gaseous stream in amounts sufficient to deposit any substantive amount of solid is also unexpected, since the gaseous stream is generated from an aqueous mixture containing only very small amounts of metal species, and the metal species remain substantially in the aqueous mixture as the aqueous mixture is degassed, oxidized, and stripped to form the gaseous stream.

It has been discovered that some of the residual metal carbonyl catalyst from the hydroformylation reaction mixture that is separated with the aqueous mixture used to extract the hydroformylation reaction mixture may collect as a volatile metal species in the gaseous stream upon degassing, oxidizing, and stripping the aqueous mixture, and that the volatile metal species, or a reaction product thereof, will deposit as a solid from the gaseous stream. For example, cobalt hydridocarbonyl ($HCo(CO)_4$) is a highly volatile species that forms from the incomplete oxidation of cobalt disproportionate salt $Co[Co(CO)_4]_2$ in the presence of small amounts of acid co-product from the hydroformylation step, and collects in the gaseous stream removed from the degasser-oxidizer-stripper tank or column when an aqueous HPA mixture is degassed, oxidized, and stripped.

The present invention provides a process for removing one or more volatile metal species, particularly volatile metal carbonyls and hydridocarbonyls, from a gaseous stream obtained by at least partially degassing an aqueous mixture separated from a hydroformylation reaction mixture. As used hereinafter the term "volatile metal species" will be referred to in the singular, however, it is to be understood that the phrase "volatile metal species" is intended to include one or more volatile metal species.

The aqueous mixture preferably contains a hydroformylation product and at least one metal species from a carbonylation catalyst. Most preferably the aqueous mixture is an aqueous solution derived by extracting a hydroformylation reaction mixture with water to separate a hydroformylation reaction product, preferably HPA, from the hydroformylation reaction mixture. The aqueous mixture may be an aqueous solution or an aqueous slurry containing at least 40% water, by weight.

The volatile metal species may be separated from the gaseous stream by contacting the gaseous stream with a liquid to wet scrub the gaseous stream, by filtering the gaseous stream with a filter having a pore size of 2 µm or less, or by contacting the gaseous stream with a suitable solid adsorbent, preferably molecular sieves. The gaseous stream from which the volatile metal species has been separated may be further processed without the volatile metal species, or a reaction product thereof, depositing as a solid material from the gaseous stream.

The aqueous mixture from which the gaseous stream is generated contains a metal species from a carbonylation catalyst and a hydroformylation product. In a preferred embodiment the metal species is a disproportionate salt of a metal carbonyl, most preferably a cobalt and/or rhodium carbonyl, and the carbonylation catalyst is a metal carbonyl, most preferably a cobalt and/or rhodium carbonyl. Most preferably the hydroformylation product in the aqueous mixture is HPA.

The aqueous mixture may be formed by 1) utilizing a carbonylation catalyst to hydroformylate an unsaturated carbon compound in the presence of syngas in an essentially water-immiscible solvent to produce a water-soluble hydroformylation product; 2) extracting the water-soluble hydroformylation product and a metal species from the carbonylation catalyst from the solvent by extracting the solvent with an aqueous extractant that is water or a water containing solution immiscible with the hydroformylation reaction solvent; and 3) separating the aqueous extractant containing the hydroformylation product and the metal species from the solvent to form the aqueous mixture. In a most preferred embodiment, the unsaturated carbon compound is ethylene oxide (EO), and the hydroformylation product is HPA.

To hydroformylate an unsaturated carbon compound, separate or combined feed streams of the unsaturated carbon compound and CO and $H_2$ (synthesis gas or "syngas") are charged to a hydroformlyation vessel, which can be a pressure reaction vessel such as a bubble column or agitated tank operated batchwise or in a continuous manner. The hydrogen and carbon monoxide will generally be introduced into the reaction vessel in a molar ratio at a range of from 1:2 to 8:1, respectively, and preferably from 1:1 to 6:1. The feed streams are contacted in the presence of a carbonylation catalyst, generally a metal carbonyl preferably selected from rhodium and/or cobalt carbonyls. The carbonylation catalyst will typically be present in the reaction mixture in an amount within the range of 0.01 to 1.0 wt. %, preferably from 0.05 to 0.5 wt. %, based on the weight of the hydroformylation reaction mixture.

The hydroformylation reaction is carried out under conditions effective to produce a hydroformylation reaction product mixture that contains significant quantities of the desired hydroformylation product, wherein the desired hydroformylation product is substantially water-soluble. As used herein, "substantially water-soluble" is defined as at least 40 wt. % soluble in water. In a preferred embodiment, the substantially water-soluble hydroformylation product is HPA and the hydroformylation reaction is carried out under continuous process conditions effective to produce a hydroformylation reaction product mixture containing a major portion of HPA and a minor portion of acetaldehyde and PDO, while maintaining the level of HPA in the reaction mixture at less than 15 wt %, preferably within the range of 3 to 10 wt %. (To provide for solvents having different densities, the desired concentration of HPA in the reaction mixture can be expressed in molarity, i.e., less than 1.5M, preferably within the range of 0.5M to 1M).

Generally, a cobalt carbonyl catalyzed hydroformylation reaction may be carried out at elevated temperatures less than 100° C., preferably 60° C. to 90° C., and most preferably 70° C. to 85° C., and rhodium carbonyl-catalyzed hydroformylations may be carried out on the order of about 10° C. higher. The hydroformylation reaction may be generally carried out at a pressure of from 3 to 35 MPa, more preferably (for process economics) at a pressure of from 7 to 25 MPa, with higher pressures preferred for greater reaction selectivity.

The hydroformylation reaction is preferably carried out in a liquid solvent inert to the reactants. By "inert" is meant that the solvent is not consumed during the course of the reaction. In general, ideal solvents for the hydroformylation process will solubilize carbon monoxide, will be essentially water-immiscible, and will exhibit low to moderate polarity such that the hydroformylation product will be solubilized to the desired concentration of at least 5 wt % under hydroformylation conditions, while significant solvent will remain as a separate phase upon water extraction. By "essentially water-immiscible" is meant that the solvent has a solubility in water at 25° C. of less than 25 wt %, so as to form a separate hydrocarbon-rich phase upon water extraction of the hydroformylation product from the hydroformylation reaction mixture.

The preferred class of solvents are alcohols and ethers which can be described by the formula

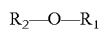

in which $R_1$ is hydrogen or $C_{1-20}$ linear, branched, cyclic, or aromatic hydrocarbyl or mono- or polyalkene oxide, and $R_2$ is $C_{1-20}$ linear, branched, cyclic or aromatic hydrocarbyl, alkoxy or mono- or polyalkylene oxide. The most preferred hydroformylation solvents are ethers such as methyl-t-butyl ether, ethyl-t-butyl ether, diethyl ether, phenylisobutyl ether, ethoxyethyl ether, diphenyl ether, and diisopropyl ether. Blends of solvent such as tetrahydrofuran/toluene, tetrahydrofuran/heptane, and t-butylalcohol/hexane can also be used to achieve the desired solvent properties. The currently preferred solvent, because of the high yields of HPA which can be achieved under moderate reaction conditions, is methyl-t-butyl ether.

To further enhance yields under moderate reaction conditions, the hydroformylation reaction mixture will preferably include a catalyst promoter to accelerate the reaction rate. Preferred promoters include lipophilic phosphonium salts and lipophilic amines, which accelerate the rate of hydroformylation without imparting hydrophobicity (water solubility) to the active catalyst. As used herein, "lipophilic" means that the promoter tends to remain in the organic phase after extraction of the hydroformylation reaction mixture with water. The promoter will generally be present in an amount within the range of 0.01 to 1.0 mole per mole of metal component of the catalyst (e.g. cobalt or rhodium carbonyl). The currently preferred lipophilic promoters are tetrabutylphosphonium acetate and dimethyldodecyl amine.

At low concentrations, water serves as a promoter for the formation of the desired carbonyl catalyst species. Optimum water levels for hydroformylation in methyl-t-butyl ether solvent are within the range of 1 to 2.5 wt %. An excessive amount of water, however, reduces selectivity to the desired hydroformylation product below acceptable levels and may induce formation of a second liquid phase.

Following the hydroformylation reaction, the hydroformylation reaction mixture containing the hydroformylation product, preferably HPA, the reaction solvent, the carbonylation catalyst, residual syngas, residual unsaturated carbon compound, and a minor amount of by-products, is cooled and passed to an extraction vessel for extraction with an aqueous liquid. The aqueous liquid, generally water and an optional miscibilizing solvent, is utilized to extract the hydroformylation reaction product mixture, and is separated from the hydroformylation reaction solvent after extraction to produce the aqueous mixture utilized in the process of the invention.

The aqueous extraction may be effected by any suitable means capable of pressurized extraction, such as mixer-settlers, packed or trayed extraction columns, or rotating disk contactors. The amount of water added to extract the hydroformylation reaction mixture will generally be such as to provide a water-mixture ratio within the range of 1:1 to 1:20, preferably 1:5 to 1:15. Extraction with a relatively small amount of water may provide an aqueous mixture containing greater than 20 wt. % hydroformylation product, preferably greater than 35 wt. % hydroformylation product, and preferably up to 60 wt. % hydroformylation product, which permits economical hydrogenation of the hydroformylation product.

The aqueous extraction is preferably carried out at a temperature within the range of 25° C. to 55° C., with lower temperatures preferred. Importantly, the aqueous extraction is carried out under positive pressure of synthesis gas. Extraction under a partial pressure of carbon monoxide from 0.4 to 7 MPa at 25° C. to 55° C. maximizes carbonylation catalyst retention in the organic phase, and minimizes the amount of carbonylation catalyst in the aqueous phase, and ultimately in the separated aqueous mixture. The extraction may be conducted under a total pressure of from 1 to 25 MPa of syngas.

After extraction, the aqueous phase is separated from the water-immiscible phase according to conventional procedures for liquid-liquid phase separation to form an aqueous mixture containing the hydroformylation product and a metal species from the carbonylation catalyst. Preferably the aqueous mixture will contain the hydroformylation product HPA and minor amounts of cobalt or rhodium carbonyls, or reaction products from cobalt and/or rhodium carbonyls such as disproportionate salts of cobalt or rhodium carbonyls. The water-immiscible phase typically will retain most of the carbonylation catalyst from the hydroformylation reaction, and is preferably recycled for further use in the hydroformylation reaction.

After the aqueous mixture containing the hydroformylation product and a metal species from the carbonylation catalyst is separated from the water-immiscible phase, the aqueous solution may be at least partially degassed, and preferably fully degassed, to generate a gaseous stream containing a volatile metal species. The volatile metal species is likely derived from the metal species of the carbonylation catalyst. The volatile metal species may be a metal carbonyl or a metal hydridocarbonyl, and most preferably is a cobalt or rhodium carbonyl or a cobalt or rhodium hydridocarbonyl. The gaseous stream will typically also contain carbon monoxide, syngas, and residual hydroformylation solvent previously entrained in the aqueous mixture.

The aqueous mixture may be degassed by reducing the pressure on the aqueous mixture. Preferably, the aqueous mixture is degassed by reducing the pressure on the aqueous mixture upon removing the aqueous mixture from the extraction apparatus to a pressure below the pressure used during the aqueous extraction. Most preferably, the reduction in pressure is sufficiently large to cause volatiles such as carbon monoxide, the volatile metal species, residual entrained hydroformylation solvent, and any other gases such as residual syngas, to flash off from the aqueous mixture. In a preferred embodiment, the extraction is conducted under a pressure of 1 to 25 MPa of syngas or carbon monoxide, and the aqueous mixture is degassed at a pressure of at most 0.2 MPa, most preferably at less than 0.15 MPa. The flow rate of gas evolved relative to liquid will depend on the amount of gas dissolved in the aqueous mixture under extraction conditions, with higher pressure resulting in a higher concentration of dissolved gas.

The aqueous mixture may also be stripped as it is degassed to more fully remove residual carbon monoxide, the volatile metal species, and a portion of the residual hydroformylation solvent. The aqueous mixture may be stripped by injecting or bubbling an inert gas into the aqueous mixture to assist in removing other gasses from the aqueous mixture. Preferably the aqueous mixture is stripped by injecting or bubbling nitrogen gas through the aqueous mixture. Any flow of stripping gas relative to aqueous liquid flow may be used to improve the removal of dissolved syngas from the aqueous mixture, beyond that which is removed via "flashing" to reduce pressure. Most typically, flow ratios of 5-20 moles/hour liquid per mole/hr of stripping gas may be employed. In a most preferred embodiment the stripping gas is contacted with the aqueous mixture in a countercurrent flow.

In a most preferred embodiment, the aqueous mixture is also preferably treated with an oxidizing agent as it is degassed and stripped. Preferably, the oxidizing agent oxidizes the metal species from the carbonylation catalyst in the aqueous mixture and the volatile metal species in the gaseous stream. Most of the oxidized metal species present and soluble in the aqueous mixture may be removed from the aqueous mixture by passing the aqueous mixture through an acidic ion exchange resin prior to passing the aqueous mixture to a hydrogenator for hydrogenation. Removal of the metal species from the aqueous mixture with the ion exchange resin prevents the metal species from poisoning the hydrogenation catalyst during subsequent hydrogenation of the hydroformylation product in the aqueous mixture. Oxidation of the volatile metal species in the gaseous stream may render the compound more easy to separate from the gaseous stream.

In one embodiment, the aqueous mixture and gaseous stream may be treated with an oxidizing gas to oxidize the metal species from the carbonylation catalyst present in the aqueous mixture and the volatile metal species in the gaseous stream. Preferably the oxidizing gas is an oxygen containing gas, and most preferably the oxidizing gas is air. Also, preferably, the aqueous mixture is treated with the oxidizing gas by contacting the aqueous mixture with the oxidizing gas in a countercurrent flow. Preferably the aqueous mixture is treated with an amount of oxidizing gas effective to oxidize most, and preferably substantially all, of the metal species from the carbonylaton catalyst in the aqueous mixture and most, and preferably substantially all, of the volatile metal species in the gaseous stream degassed from the aqueous mixture. Most preferably, the oxidizing gas is diluted with an inert component such as nitrogen to maintain a composition outside the flammable limits for the resulting gas mixture. A preferred operation will employ a flow ratio of 5-20 moles/hour aqueous liquid per mole/hour of combined stripping and oxidizing gas. Concentrations of oxygen in the stripping gas should preferably be less than 5% molar to avoid flammable compositions.

In another embodiment, the aqueous mixture and gaseous stream may be treated with an oxidizing liquid to oxidize the metal species from the carbonylation catalyst present in the aqueous mixture and the volatile metal species in the gaseous stream. Preferably the oxidizing liquid is either nitric acid or hydrogen peroxide. The aqueous mixture and gaseous stream may be treated with the oxidizing liquid in a countercurrent flow or by otherwise being mixed with the aqueous mixture. Preferably the aqueous mixture is treated with an amount of oxidizing liquid effective to oxidize most, and preferably substantially all, of the metal species from the carbonylaton catalyst in the aqueous mixture and most, and preferably substantially all, of the volatile metal species in the gaseous stream degassed from the aqueous mixture. In general, this can be accomplished by supplying an amount of oxidant in stoichiometric excess over the total moles of metal species present in the aqueous mixture prior to degassing and stripping.

Applicants believe that contacting the aqueous mixture with an oxidizing agent causes a small portion of the metal species from the carbonylation catalyst present in the aqueous solution to become volatile and enter the gaseous stream. For example, the cobalt disproportionate salt $Co[Co(CO)_4]_2$ may be present in the aqueous mixture from a cobalt carbonyl catalyst utilized as the hydroformylation catalyst in the hydroformylation of ethylene oxide to HPA. The cobalt disproportionate salt is in equilibrium with volatile cobalt hydridocarbonyl $HCo(CO)_4$ in the presence of 3-hydroxypropionic acid, which is present in the aqueous mixture as a side product of the hydroformylation reaction. The equilibrium disfavors formation of the strongly acidic cobalt hydridocarbonyl. Oxidizing and stripping the aqueous mixture in the presence of a stabilizing pressure of off-gassing carbon monoxide, however, can drive the equilibrium towards the formation of the cobalt hydridocarbonyl, allowing the volatile cobalt hydridocarbonyl to escape in the gaseous stream.

Temperature may be used to optimize oxidation of the volatile metal species from the gaseous stream. The temperature may be raised during the oxidation step via addition of steam, hot water, or other means, to accelerate the oxidation of the volatile component. Preferably the temperature at which the oxidizing agent is contacted with the aqueous mixture and the gaseous stream is from 50° C. to 100° C. to accelerate the oxidation of the volatile metal species.

The aqueous mixture may be degassed, and optionally stripped and oxidized, in a conventional tank or column capable of accepting a pressurized liquid, venting the gaseous stream as an off-gas, and permitting the degassed aqueous mixture to be removed from the column or tank. If, as preferred, the aqueous mixture is to be stripped and oxidized, the tank or column must provide inlets for injecting a stripping gas, and an oxidizing gas or liquid into the aqueous solution.

The volatile metal species is separated from the gaseous stream produced by degassing the aqueous mixture in a manner effective to inhibit or prevent deposition of a solid material from the gaseous stream after the volatile metal species is removed from the gaseous stream. In a preferred embodiment the volatile metal species is separated from the gaseous stream by contacting the gaseous stream with a liquid or solid, and collecting the volatile metal species, or a reaction product thereof, apart from the gaseous stream.

The liquid or solid for separating the volatile metal species from the gaseous stream should be selected to be effective for removing the volatile metal species from the gaseous stream. In one embodiment an aqueous trapping liquid in which the volatile metal species is soluble, or with which the volatile metal species will react to form a non-gaseous reaction product, is used to separate the volatile metal species from the gaseous stream. Preferably the aqueous trapping liquid is water, and more preferably the aqueous trapping liquid is the aqueous mixture from the hydroformylation reaction mixture extraction, which optionally has been degassed, oxidized, and stripped. Optionally, the aqueous trapping liquid is a basic solution, preferably an alkaline solution such as potassium hydroxide or sodium hydroxide. Volatile metal hydridocarbonyls such as cobalt hydridocarbonyl may be effectively removed from the gaseous stream with water or the aqueous mixture extracted from the hydroformylation reaction mixture, and are particularly effectively removed from the gaseous stream by an aqueous basic solution since volatile metal hydridocarbonyls are strongly acidic, and react with the base to form salts. Typical flow ratios would entail treating 2-100 parts by weight of gas with one part of trapping liquid.

In another embodiment, a liquid organic solvent in which the volatile metal species is soluble is used to separate the volatile metal species from the gaseous stream. Preferably the liquid organic solvent is MTBE. Volatile metal carbonyls that have not been oxidized and are not salts, such as cobalt and rhodium carbonyl, may be effectively removed from the gaseous stream with MTBE. An organic solvent in which the volatile metal species is soluble may be most effectively used to separate the volatile metal species from the gaseous stream when the aqueous mixture is subjected to little or no oxidation. Typical flow ratios preferably would entail treating 2-100 parts by weight of gas with one part of trapping organic liquid.

In a most preferred embodiment the aqueous mixture from the hydroformylation reaction mixture extraction—which optionally has been degassed, oxidized, and stripped—is used as the liquid trapping agent to separate the volatile metal species from the gaseous stream. The aqueous mixture is particularly preferred because it contains a significant level of organic compounds so that the aqueous mixture may effectively remove both volatile metal hydridocarbonyls and non-oxidized volatile metal carbonyls from the gaseous stream.

The gaseous stream containing the volatile metal species may be contacted with the trapping liquid to separate the volatile metal species from the gaseous stream using a conventional apparatus commonly used to contact and mix a liquid with a gas. It is particularly preferred that the apparatus used for contacting the gaseous stream and the trapping liquid is amenable to operation in the presence of solids. Solids may form when the volatile metal species in the gaseous stream contacts the liquid and the volatile metal species is separated from the gaseous stream.

In a preferred embodiment, a conventional commercially available venturi scrubber is used to contact the gaseous stream with a trapping liquid to separate the volatile metal species from the gaseous stream. Venturi scrubbers may be designed to accommodate a wide range of liquid/gas flows, as well as the solids which may form due to trapping the volatile metal species. Typically, the liquid flow would be designed to maintain a concentration of solids of less than one percent of the total flow.

In another preferred embodiment, a conventional commercially available tray or plate column is used to contact the gaseous stream containing the volatile metal species with a trapping liquid to separate the volatile metal species from the gaseous stream. A trapping liquid flow is preferably provided in an amount effective to maintain a concentration of solids below about one percent. Flow of the gaseous stream in the column is preferably regulated to provide for sufficient holdup of liquid on the trays or plates to allow effective contacting of the gas phase with the trapping liquid. Variation in column diameter and tray or plate design allows these conditions to be met simultaneously, once the expected flow rate of volatile metal species is known. Other means of contacting the trapping liquid with the gaseous stream beyond those described above include spray towers, bubble columns, and packed columns.

In a most preferred embodiment, the aqueous mixture formed by aqueous extraction of a hydroformylation reaction mixture is used as the trapping liquid to separate the volatile metal species from the gaseous stream after the aqueous mixture is degassed, stripped, and oxidized. Most preferably, the aqueous mixture is degassed, stripped, and oxidized in a plate or trayed column, and then is re-circulated through the column to contact the gaseous stream to separate the volatile metal species from the gaseous stream.

Pressurized aqueous mixture from extraction of a hydroformylation reaction mixture may be delivered centrally between the top and bottom of a degassing, stripping, and oxidizing column to degas, strip, and oxidize the aqueous mixture and to permit re-circulated degassed, stripped, and oxidized aqueous mixture to separate the volatile metal species from the gaseous stream. The pressurized aqueous mixture is degassed upon entry into the lower pressure column. The off-gassed gaseous stream formed by degassing the aqueous mixture flows upward through the column from the centrally located entry area to the top of the column. The degassed aqueous mixture flows from the centrally located entry area down toward the bottom of the column. Air and nitrogen may be injected into the aqueous mixture at or near the bottom of the column, which is preferably arranged so the air and nitrogen flow upwards through the column countercurrent to the downward flowing aqueous mixture. Upon reaching the bottom, or near the bottom, of the column a portion of the aqueous mixture—having been degassed, stripped, and oxidized—may be removed from the column and eluted through an acidic ion exchange resin to remove oxidized water soluble metal species therein, and then may be hydrogenated.

Another portion of the degassed, stripped, and oxidized aqueous mixture may be re-circulated from the bottom, or near the bottom, of the column to the top, or near the top, of the column, whereupon the re-circulated aqueous mixture flows downward through the column from the top, or near the top, to the bottom, or near the bottom, of the column. The re-circulated aqueous mixture contacts the upward-flowing gaseous stream as the re-circulated aqueous mixture flows down the column. The re-circulated aqueous mixture acts as a trapping liquid and separates the volatile metal species from the gaseous stream. The gaseous stream may then be removed from the top of the column and treated to separate any residual hydroformylation solvent therein. Upon reaching the bottom of the column, the re-circulated aqueous mixture may be re-circulated again, or may be removed from the column for elution through an acidic ion exchange resin and hydrogenation.

In another embodiment of the invention, the volatile metal species may be also be separated from the gaseous stream by oxidizing the gaseous stream and mechanically filtering the oxidized gaseous stream in a manner effective to inhibit or prevent deposition of a solid material from the gaseous stream after the volatile metal species is removed from the gaseous stream. Preferably the gaseous stream is oxidized by contact with an oxygen containing gas, preferably air. A filtration system may be set up that is effective to remove most, if not all, of the volatile metal species or its reaction products from the oxidized gaseous stream. In one embodiment, the volatile metal species is separated from the gaseous stream by passing the oxidized gaseous stream through a filter having a pore size of 2 µm or less, preferably 1 µm or less. A preferred filter having a pore size of 1 µm or less is a commercially available HEPA submicron filter formed of glass wool.

In a particularly preferred embodiment, a series of two or more filters are used to separate the volatile metal species from the gaseous stream. The gaseous stream may be passed through a first filter having a pore size of from 2 to 4 μm, and then may be passed through a final filter having a pore size of 1 μm or less, preferably a HEPA submicron filter formed of glass wool. Other filters may be used between the first and final filters, where the other filters preferably have pore sizes between the pore size of the first filter and the final filter.

In a preferred embodiment, the filters are washed at least intermittently while passing the gaseous stream through the filters. The intermittent wash is used to clean the filters of solids that are soluble in the wash, and that may have deposited on the filters as a result of separating the volatile metal species from the gaseous stream. An aqueous wash is preferred to wash the filters, and an aqueous alkaline wash is most preferred.

If a filter is used to separate the volatile metal species or its reaction products from the gaseous stream, the filter should be located very near the gas outlet from the degassing column or tank through which the gaseous stream exits the degassing column or tank. Locating the filter directly adjacent the gas outlet from the degassing tank or column permits the filter to separate the volatile metal species or its reaction products from the gaseous stream without the volatile metal species or its reaction products depositing as a solid in the connecting lines or other process components such as compressors or chillers.

In a most preferred embodiment, the volatile metal species is separated from the gaseous stream by contacting the gaseous stream with a trapping liquid, as described above, followed by passing the gaseous stream through at least one mechanical filter, also as described above.

In another embodiment of the invention, the volatile metal species may be also be separated from the gaseous stream by contacting the gaseous stream with an adsorbent solid effective for adsorbing the volatile metal species and/or its reaction products. Preferably the volatile metal species is separated from the gaseous stream by passing the gaseous stream over a fixed bed of a material effective for adsorbing the volatile metal species and/or its reaction products. Silica, alumina, or silica-alumina adsorbents, preferably molecular sieves, may be used for this purpose. In a preferred embodiment, the material used in the fixed bed for adsorbing the volatile metal species and/or its reaction products, is commercially available molecular sieves, preferably molecular sieves 13X adsorbent. Passing the gaseous stream through a long bed length of the absorbent material is preferred over a short bed length to effectively separate the volatile metal species from the gaseous stream. An appropriate bed length can be determined by measuring the amount of the volatile metal species remaining in the gaseous stream after passing through the bed at a specific flow rate of the gaseous stream, and adjusting the bed length to optimize the bed length size for removing the volatile metal species from the gaseous stream.

Preferably, the gaseous stream is oxidized to oxidize the volatile metal species before passing the gaseous stream over the fixed bed of adsorbent material, thereby increasing the amount of the volatile metal species and/or its reaction products likely to be adsorbed on the adsorbent material. The gaseous stream may be oxidized as described above by contacting the gaseous stream with an oxidizing agent such as air or an oxidizing liquid, under conditions to provide a stoichiometric excess of oxidation relative to the amount of volatile metal species to be removed.

Temperature may be used to optimize removal of the volatile metal species from the gaseous stream. If oxidation does not go to completion, then a low temperature is preferred for the subsequent trapping or adsorption step, to induce the volatile metal species to condense from the gaseous stream into a liquid or onto an adsorbent. For example, cobalt hydridocarbonyl has a boiling point of 47° C., so it is preferable to use a trapping liquid having a temperature of 40° C. or lower to separate cobalt hydridocarbonyl from the gaseous stream. In a preferred embodiment, a chilled trapping liquid used to separate the volatile metal species from the gaseous stream, where the chilled trapping liquid preferably has a temperature of from 5° C. to 15° C.

Referring now to FIG. 1, a preferred embodiment for conducting the process of the present invention is shown. A carbon monoxide/syngas pressurized aqueous solution under a pressure of at least 1 MPa and containing a metal species from a carbonylation catalyst, a hydroformylation product, carbon monoxide, syngas, and a residual organic solvent may be charged to a degasser-stripper-oxidizer (DSO) column 11 through an inlet 13 located centrally between the top 15 and bottom 17 of the DSO column 11. The aqueous solution is preferably an aqueous extract of a hydroformylation reaction performed using a carbonylation catalyst, most preferably a cobalt carbonyl catalyst. The DSO column 11 is preferably a trayed or plate column. The DSO column 11 is maintained at a significantly lower pressure than the entering aqueous solution—preferably less than 0.15 MPa—so that carbon monoxide, a volatile metal species, syngas, and residual organic solvent flash off from the aqueous solution upon entering the column 11 and form a gaseous stream that flows from the inlet 13 towards the top 15 of the column 11.

The DSO column 11 may be filled with the aqueous solution except for an overhead space 19 near the top 15 of the DSO column 11. The DSO column 11 may have a bottoms outlet 21 through which degassed, stripped and oxidized aqueous solution may exit the DSO column 11. An aqueous solution recycle feed line 23 may extend from near the bottom 17 to near the top 15 of the DSO column 11. Aqueous solution entering the DSO column 11 flows from the inlet 13 toward the bottom 17 of the DSO column 11. At the bottom 17 of the DSO column 11 a portion of the aqueous solution may exit the DSO column 11 through the bottoms outlet 21, and a portion of the aqueous solution may enter the recycle feed line 23. A pump 25 may be used to pump the aqueous solution through the recycle feed line 23 from near the bottom 17 to the near the top 15 of the column 11. Aqueous solution entering the DSO column 11 from the recycle feed line 23 then may flow down through the column 11 to the bottom 17 of the column 11.

Air and nitrogen may be injected into the DSO column 11 through ports 27 and 29, respectively, at the bottom 17 of the column 11. The air, nitrogen, and gaseous stream flow upward through the column 11, collect in the overhead space 19, and exit the column 11 through a gas outlet 31. The air and nitrogen flow upward, countercurrent to the downward flowing aqueous solution, and oxidize and strip the aqueous solution.

The aqueous solution entering the column 11 from the recycle feed line 23 contacts the gaseous stream flowing upwards from the inlet 13 and separates the volatile metal species from the gaseous stream. The aqueous solution entering the column 11 from the recycle feed line 23 is degassed of carbon monoxide, syngas, and residual solvent and is rich in oxygen and nitrogen. The aqueous solution entering the column 11 from the recycle feed line 23 acts to oxidize the gaseous stream flowing upwards from the inlet 13, at least partially oxidizing the volatile metal species. The length of the column from the inlet 13 to the point at which the aqueous solution reenters the column 11 through the recycle feed line is preferably long enough to provide sufficient contact time between the aqueous solution and the gaseous stream to remove substantially all of the volatile metal species and its reaction products from the gaseous stream before the gaseous stream arrives at the overhead space 19.

The gaseous stream, oxygen, and nitrogen exiting the column 11 through the gas outlet 31 are then preferably compressed in a compressor (not shown) and optimally chilled with chilled brine in a solvent recovery system (not shown) to recover any residual solvent present in the gaseous stream. The gaseous stream deposits little or no solids in the piping, compressor, or solvent recovery system since the gaseous stream contains little or no volatile metal species and/or its reaction product(s).

The aqueous solution exiting the column through bottoms outlet 21 may be passed through an acid ion exchange resin bed (not shown) to remove the oxidized metal species that are soluble in the aqueous solution. The aqueous solution may then be passed to a hydrogenation reactor (not shown) for hydrogenation of the hydroformylation reaction product, preferably HPA, to a hydrogenation product, preferably PDO.

Figure 2:
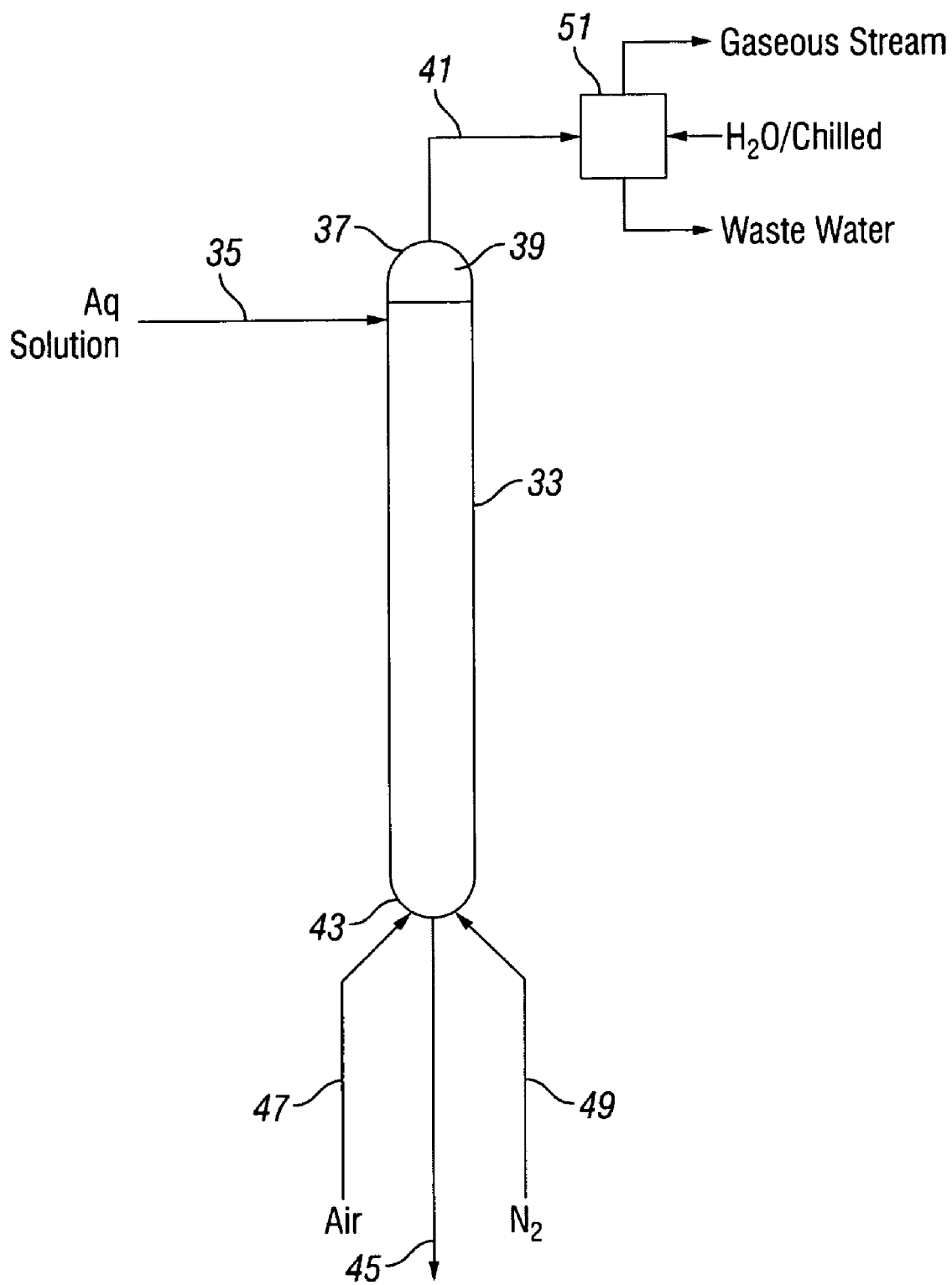
FIG. 2 is a schematic representation of a degasser-stripper-oxidizer column and a scrubber for use in accordance with the process of the present invention.

Referring now to FIG. 2, another preferred embodiment for conducting the process of the present invention is shown. A carbon monoxide/syngas pressurized aqueous solution under a pressure of at least 1 MPa containing a metal species from a carbonylation catalyst, a hydroformylation product, carbon monoxide, syngas, and a residual organic solvent may be charged to a degasser-stripper-oxidizer (DSO) column 33 through an inlet 35 located near the top 37 of the DSO column 33. The aqueous solution is preferably an aqueous extract of a hydroformylation reaction performed using a carbonylation catalyst, most preferably a cobalt carbonyl catalyst. The DSO column 33 is preferably a trayed or plate column. The DSO column 33 is preferably maintained at a significantly lower pressure than the entering aqueous solution—preferably less than 0.15 MPa—so that the carbon monoxide, a volatile metal species, syngas, and residual organic solvent flash off from the aqueous solution upon entering the column 11, and form a gaseous stream that collects in an overhead space 39 near the top 37 of the DSO column 33 and exits the column 33 through a gas outlet 41.

The DSO column 33 is preferably filled with the aqueous solution except for the overhead space 39. Aqueous solution entering the DSO column 33 flows from the inlet 35 towards the bottom 43 of the DSO column, and exits the column 33 through a bottoms outlet 45. Air and nitrogen may be injected into the DSO column 33 through ports 47 and 49, respectively, at the bottom 43 of the column 33. The air and nitrogen flow upwards through the column 33 countercurrent to the flow of the aqueous solution, and oxidize and strip the aqueous solution. The air and nitrogen collect in the overhead space 39 along with the gaseous stream, and exit the column 33 through the gas outlet 41 along with the gaseous stream. The oxygen in the air serves to oxidize the gaseous stream upon contacting the gaseous stream.

The air, nitrogen, and gaseous stream are directed from the gas outlet 41 into a venturi scrubber 51. Chilled water, preferably having a temperature of 10-15° C. is also directed into the venturi scrubber 51, wherein the chilled water stream is contacted with the gaseous stream, air and nitrogen in the scrubber 51. The chilled water stream separates the volatile metal species from the gaseous stream, air, and nitrogen. The gaseous stream, air, and nitrogen are then directed from the venturi scrubber 51 to a compressor (not shown), and then to a condenser (not shown) wherein a chilled brine solution is used to separate residual hydroformylation solvent from the gaseous stream. The water, after contacting the gaseous stream, is directed out of the scrubber 51 as a waste water stream and is passed through a filter (not shown) to remove solids from the water, and then may be cycled back into the scrubber 51.

The aqueous solution exiting the column 33 through bottoms outlet 45 may be passed through an acid ion exchange resin bed (not shown) to remove the oxidized metal species that are soluble in the aqueous solution. The aqueous solution may then be passed to a hydrogenation reactor for hydrogenation of the hydroformylation reaction product, preferably HPA, to a hydrogenation product, preferably PDO.

EXAMPLE 1

An aqueous solution was produced by continuously hydroformlyating ethylene oxide with synthesis gas (CO and $H_2$) under a pressure of 7 to 15 MPa at a temperature of 60° C. to 100° C. in the presence of a dicobaltoctacarbonyl catalyst in a methoxy-t-butyl ether solvent, followed by continuous aqueous extraction of the reaction mixture to produce the aqueous solution. The aqueous extraction was conducted at 10 MPa and 20° C. to 45° C. The aqueous solution contained from 12 wt. % to 35 wt. % 3-hydroxypropionaldehyde, between 50 and 200 ppm cobalt, and traces of acetaldehyde, MTBE, and 3-hydroxypropionic acid. The aqueous solution was passed into a degasser vessel that was a 5.1 cm diameter by 20.3 cm tall sight glass operated at the half-full mark of 200 ml. Pressure in the degasser was maintained by synthesis gas released from the aqueous solution upon depressurization, with excess gas vented from the top of the degasser vessel. Pressure was measured by a pressure transducer, and controlled to 0.2 to 0.3 MPa via an automated control valve on the gas-phase vent. A separate pressure transducer measured differential pressure associated with liquid level in the degasser vessel. Liquid level was controlled by a separate control valve for liquid outflow at the bottom of the vessel.

Liquid flow from the degasser vessel was routed to the top tray of a glass stripper column, where the column was a 5.1 cm diameter non-insulated 10-tray Oldershaw column operated with a maximum of 0.48 cm liquid loading per tray. A mixture of 3% $O_2$ in $N_2$ gas was fed counter to the liquid flow from the bottom of the column at flows of 14.2 to 56.6 liter/hr. The aqueous solution fed at the top of the column cascaded downward along the trays and exited at the bottom of the column to be routed to cobalt ion exchange removal beds. The stripper column was operated at 0.12 to 0.15 MPa total pressure by backpressure control on stripping gas exiting at the top of the column.

The degasser and stripper columns were operated continuously for a period of five weeks, at which time the overhead vent line from the degasser plugged with green solids. Analysis of the solids indicated the principle species to be cobalt. Similar brown-green solids were observed at the top section of the glass Oldershaw column above the liquid entry point, and again analyzed as cobalt.

These results show that volatile cobalt species are produced during degassing and stripping of an aqueous solution produced by water extraction of a hydroformylation mixture employing cobalt carbonyl as the catalyst.

EXAMPLE 2

Direct synthesis of cobalt hydridocarbonyl was performed entailing the reaction of dicobaltoctacarbonyl with pyridine to form a disproportionate salt, and volumetric addition of this salt to sulfuric acid to generate cobalt hydridocarbonyl. Direct synthesis was necessary to produce the volatile cobalt species observed during degassing and stripping of an aqueous extract of a cobalt carbonyl catalyzed hydroformylation mixture for the purpose of testing various means of trapping the volatile cobalt species.

3 grams of dicobalt octacarbonyl were dissolved in 20 grams of pyridine under a nitrogen blanket, allowing for degassing of evolved carbon monoxide. The mixture was charged to a nitrogen flushed buret. The buret was attached to a 250 ml. 3-necked flask provided with an outlet tube and an inlet tube constricted at the tip and inserted to nearly the bottom of the flask. The top of the buret and the inlet tube were connected through a T-tube arrangement. A solution of 25 ml of 18 M sulfuric acid and 75 ml of water was cooled to −17.8° C. to −15° C. and then was placed in the 250 ml 3-necked flask under a nitrogen blanket, and the flask was immersed in an ice bath. The flask was then purged with a 2:1 mixture of hydrogen/carbon monoxide ("syngas") at a flow rate of about 300 ml/min. The pyridine/dicobalt octacarbonyl solution was then added drop-wise to the acidic solution in the flask for about 45 to 60 minutes to produce from 1.61 to 1.91 g of cobalt hydridocarbonyl.

EXAMPLE 3

Example 3 was conducted to show that water, steam, MTBE, DSO bottoms, and DSO bottoms are effective to separate a cobalt hydridocarbonyl compound from a gaseous stream. Synthesis gas (CO/H$_2$) was purged at 3-10 ml/min through a 300 ml flask containing cobalt hydridocarbonyl synthesized according to the process described above in Example 2. A gas stream containing the cobalt hydridocarbonyl and the synthesis gas was routed to a first trap flask with a dip tube in the trap flask placed to ensure contact between the gas stream and the contents of the trap flask, where the contents of the first trap flask were either water, methoxy-t-butyl ether, 90° C. steam, or DSO bottoms, where the DSO bottoms were provided by degassing, stripping, and oxidizing an aqueous extract of a 3-hydroxypropionaldehyde hydroformylation reaction mixture containing a cobalt carbonyl hydroformylation catalyst. The gas stream was then routed from the first trap flask to a second trap flask containing 1 N potassium hydroxide solution, a highly effective trapping liquid for cobalt hydridocarbonyl. The gas stream was injected into the second trap flask by a dip tube to ensure contact of the gas stream with the 1 N potassium hydroxide. Air was added to the gas stream prior to the first trap flask when the first trap flask contained water or steam. Nitrogen gas was also added to the gas stream prior to the first trap flask when the first trap flask contained steam. Efficiency of the tested trapping liquid was best gauged by the percent cobalt removed in the first trap flask relative to the total amount of cobalt trapped in the first and second trap flasks. The results are shown below in Table 1.

TABLE 1

| Trapping substance - Trap 1 | Water | MTBE | Steam | DSO Bottoms |
|---|---|---|---|---|
| Syngas (ml/min) | 10 | 3 | 3 | 10 |
| Air (ml/min) | 10 | 0 | 7.5 | 10 |
| N$_2$ (ml/min) | 0 | 0 | 7.5 | 0 |
| Trap 1 weight of trapping substance in trap (g) | 5 | 5 | 5 | 4 |
| Cobalt Trapped in Trap 1 (ppm) | 862 | 9709 | 702 | 970 |
| Cobalt Trapped in Trap 2 (ppm) | 365 | 1 | 26 | 36 |
| % Co Captured Trap 1 v. Traps 1 + 2 | 70.3 | 99.9 | 96.4 | 96.4 |

The results indicate that water is effective to trap cobalt from an oxidized cobalt hydridocarbonyl feed stream with at least 70% efficiency, and that MTBE, DSO bottoms, and steam are effective to trap cobalt from an unoxidized cobalt hydridocarbonyl feed stream at near 100% efficiency.

EXAMPLE 4

Example 4 was conducted to show that mechanical filtration with microfilters is effective to separate a cobalt hydridocarbonyl compound from a gaseous stream. Synthesis gas (CO/H$_2$) was purged at 10 ml/min through a 300 ml flask containing cobalt hydridocarbonyl synthesized according to the process described above in Example 2. A gas stream containing the cobalt hydridocarbonyl and the synthesis gas was routed through a microfilter. The gas stream was then routed from the microfilter to a trap flask containing 1 N potassium hydroxide solution, a highly effective trapping liquid for cobalt hydridocarbonyl. The gas stream was injected into the trap flask by a dip tube to ensure contact of the gas stream with the 1 N potassium hydroxide. Air was added to the gas stream prior to the microfilter. In a first test, the filter was a 2 μm filter. In a second test, the microfilter was glass wool.

Efficiency of the tested filters was best gauged by the percent cobalt removed in the filter relative to the total amount of cobalt trapped in the trap flask. The results are shown below in Table 2.

TABLE 2

| Trapping filter | 2 μm filter | Glass wool |
|---|---|---|
| Syngas (ml/min) | 10 | 10 |
| Air (ml/min) | 10 | 10 |
| N$_2$ (ml/min) | 0 | 0 |
| Cobalt Trapped in Filter (ppm) | 5000 | 650 |
| Cobalt Trapped in Trap (ppm) | 15 | 72 |
| % Co Captured Filter v. Filter + Trap | 99.7 | 90.0 |

The results indicate that microfilters are effective to trap cobalt from an oxidized cobalt hydridocarbonyl feed stream with at least 90% efficiency.

EXAMPLE 5

Example 5 was conducted to show that a fixed bed of an adsorbent material is effective to separate a cobalt hydridocarbonyl compound from a gaseous stream. Synthesis gas (CO/H$_2$) was purged at 10 ml/min through a 300 ml flask containing cobalt hydridocarbonyl synthesized according to the process described above in Example 2. A gas stream containing the cobalt hydridocarbonyl and the synthesis gas was routed over a fixed bed of molecular sieves (13X) at a VHSV flow rate of either 1200 l/h or 2400 l/h. Two fixed beds of molecular sieves were employed in parallel with a timer valve used to distribute flow of the gas stream between the two beds in 1 minute intervals. The parallel arrangement of beds with a periodic timed flow of the volatile cobalt gas over the beds ensured even distribution of the cobalt over the beds. Each fixed bed of molecular sieves was 4 cm long and contained 0.5 g of molecular sieves in a 0.5 ml volume. The gas stream was then routed from the fixed beds of molecular sieves to a trap flask containing 1 N potassium hydroxide solution, a highly effective trapping liquid for cobalt hydridocarbonyl, to measure any cobalt breakthrough from the fixed beds. The gas stream was injected into the trap flask by a dip tube to ensure contact of the gas stream with the 1 N potassium hydroxide.

Two sets of runs were conducted, one measuring the volatile cobalt adsorbtion effect of fixed beds of molecular sieves (13X) when the gaseous stream was not subject to oxidation by air, and the second measuring the same effect when the gaseous stream was subject to oxidation by air. Air was added to the gas stream prior to the molecular sieve fixed beds in the oxidation test runs.

Efficiency of the fixed beds of molecular sieves to separate cobalt from the gas stream was measured by percentage of cobalt adsorbed on the molecular sieves relative to the cobalt feed from the gas stream. The results are shown below in Table 3.

TABLE 3

|  | Syngas (ml/min) | VHSV (1/h) | MolSiev Cobalt adsorption - % of feed |
| --- | --- | --- | --- |
| Bed 1-unoxidized feed | 10 | 1200 | 100 |
| Bed 2-unoxidized feed | 10 | 1200 | 99.1 |
| Bed 1-oxidized feed | 10 | 2400 | 100 |
| Bed 2-oxidized feed | 10 | 2400 | 100 |

The results show that fixed bed adsorption using molecular sieves is effective to trap volatile cobalt from both an unoxidized and an oxidized cobalt hydridocarbonyl feed stream.

EXAMPLE 6

A prophetic example is provided derived from the results and conclusions of Examples 1 and 3, illustrating a process in accordance with the present invention. An aqueous solution is produced by continuously hydroformlyating ethylene oxide with synthesis gas (CO and $H_2$) under a pressure of 7 to 15 MPa at a temperature of 60° C. to 100° C. in the presence of a dicobaltoctacarbonyl catalyst in a methoxy-t-butyl ether solvent, followed by continuous aqueous extraction of the reaction mixture to produce the aqueous solution. The aqueous extraction is conducted at 10 MPa and 20° C. to 45° C. The aqueous solution contains from 12 wt. % to 35 wt. % 3-hydroxypropionaldehyde, between 50 and 200 ppm cobalt, and traces of acetaldehyde, MTBE, and 3-hydroxypropionic acid.

The aqueous solution is passed to a degasser, stripper, oxidizer column where it is degassed and stripped with a stream of oxygen and nitrogen gas at a reduced pressure relative to the pressure at which the aqueous solution enters the degasser, stripper, oxidizer column. A gaseous stream from the stripped and degassed aqueous solution is routed to a first trap flask with a dip tube in the trap flask placed to ensure contact between the gaseous stream and the contents of the trap flask, where the contents of the first trap flask are either water, methoxy-t-butyl ether, 90° C. steam, or DSO bottoms, where the DSO bottoms are the stripped and degassed aqueous solution. The gaseous stream is then routed from the first trap flask to a second trap flask containing 1 N potassium hydroxide solution, a highly effective trapping liquid for cobalt hydridocarbonyl. The gaseous stream is injected into the second trap flask by a dip tube to ensure contact of the gaseous stream with the 1N potassium hydroxide solution. Efficacy of the trapping medium is measured by comparison of the percent cobalt removed in the first trap flask relative to the second trap flask. The trapping media are effective to trap at least 70 wt. % of the cobalt from the gaseous stream.

What is claimed is:

1. A process for inhibiting or preventing deposition of a solid material from a gaseous stream obtained from an aqueous mixture separated from a hydroformylation reaction mixture, comprising:

separating a volatile metal species from a gaseous stream obtained by at least partially degassing an aqueous mixture separated from a hydroformylation reaction mixture.

2. The process of claim 1 wherein said volatile metal species is a metal hydridocarbonyl.

3. The process of claim 2 wherein said metal hydridocarbonyl is a cobalt hydridocarbonyl or a rhodium hydridocarbonyl.

4. The process of claim 1 wherein said gaseous stream contains an ether.

5. The process of claim 4 further comprising compressing and chilling said gaseous stream after separation of the volatile metal species from the gaseous stream to separate the ether from the gaseous stream.

6. The process of claim 1 wherein the aqueous mixture is at least partially degassed by reduction of pressure on the aqueous mixture.

7. The process of claim 1 wherein an oxidizing agent is contacted with the aqueous mixture and the gaseous stream.

8. The process of claim 7 wherein the oxidizing agent is an oxygen containing gas.

9. The process of claim 1 wherein said volatile metal species is separated from the gaseous stream by contacting the gaseous stream with a trapping liquid.

10. The process of claim 9 wherein the trapping liquid is the aqueous mixture separated from the hydroformylation reaction mixture.

11. The process of claim 9 wherein the gaseous stream is passed through a filter having a pore size of 2 microns or less after being contacted with a trapping liquid.

12. The process of claim 1 wherein the volatile metal species is separated from the gaseous stream by passing the gaseous stream through a filter having a pore size of 2 microns or less.

13. The process of claim 1 wherein the volatile metal species is separated from the gaseous stream by contacting the gaseous stream with an adsorbent solid.

14. The process of claim 13 wherein said adsorbent solid comprises molecular sieves.

* * * * *